(12) United States Patent
Bao et al.

(10) Patent No.: US 10,544,811 B2
(45) Date of Patent: Jan. 28, 2020

(54) PHOTOACOUSTIC LAYER DISPOSED ON A SUBSTRATE GENERATING DIRECTIONAL ULTRASOUND WAVES

(71) Applicants: Jiming Bao, Pearland, TX (US); Feng Lin, Houston, TX (US); Zhuan Zhu, Houston, TX (US); Qiuhui Zhang, Houston, TX (US); Yanan Wang, Houston, TX (US); Zhiming Wang, Katy, TX (US)

(72) Inventors: Jiming Bao, Pearland, TX (US); Feng Lin, Houston, TX (US); Zhuan Zhu, Houston, TX (US); Qiuhui Zhang, Houston, TX (US); Yanan Wang, Houston, TX (US); Zhiming Wang, Katy, TX (US)

(73) Assignee: UNIVERSITY OF ELECTRONIC SCIENCE AND TECHNOLOGY OF CHINA, Chengdu, Sichuan (CN)

( * ) Notice: Subject to any disclaimer, the term of this patent is extended or adjusted under 35 U.S.C. 154(b) by 150 days.

(21) Appl. No.: 15/901,242

(22) Filed: Feb. 21, 2018

(65) Prior Publication Data

US 2018/0238358 A1  Aug. 23, 2018

Related U.S. Application Data

(60) Provisional application No. 62/461,371, filed on Feb. 21, 2017.

(51) Int. Cl.
*F15C 1/02* (2006.01)
*F15D 1/02* (2006.01)
*G10K 15/04* (2006.01)
*G10K 11/34* (2006.01)
*G01N 21/17* (2006.01)
*G01N 29/24* (2006.01)

(52) U.S. Cl.
CPC ............ *F15D 1/02* (2013.01); *G01N 21/1702* (2013.01); *G01N 29/2418* (2013.01); *G10K 11/34* (2013.01); *G10K 15/046* (2013.01)

(58) Field of Classification Search
CPC ........ F15D 1/02; G10K 11/34; G10K 15/046; G01N 29/2418; G01N 21/1702
USPC ................ 137/827, 828, 842, 81.2; 181/113; 356/484; 601/15
See application file for complete search history.

(56) References Cited

U.S. PATENT DOCUMENTS

| 3,194,640 A * | 7/1965 | Nesh ................... G11B 5/70647 23/293 R |
| 3,614,069 A * | 10/1971 | Murry ................. B01F 11/0208 366/119 |
| 4,512,197 A * | 4/1985 | von Gutfeld ...... G01N 29/2418 73/601 |

(Continued)

*Primary Examiner* — Minh Q Le
(74) *Attorney, Agent, or Firm* — Conley Rose, P.C.

(57) ABSTRACT

Disclosed is a system including a substrate having a first side and a second side and a layer of photoacoustic material disposed on the first side of the substrate. The layer of photoacoustic material is configured to generate a directional ultrasound wave in response to a laser beam impinging on the layer. A conduit may be coupled to the housing and have an opening adjacent to the layer of photoacoustic material; the directional ultrasound wave may be directed through fluid that is contained in the conduct to generate a liquid jet in a liquid.

23 Claims, 6 Drawing Sheets

(56) References Cited

U.S. PATENT DOCUMENTS

| | | | |
|---|---|---|---|
| 5,929,337 A * | 7/1999 | Collins | B65B 57/00 |
| | | | 209/590 |
| 6,029,518 A | 2/2000 | Oeftering | |
| 6,210,128 B1 | 4/2001 | Rife et al. | |
| 6,948,843 B2 | 9/2005 | Laugharn, Jr. et al. | |
| 7,757,561 B2 * | 7/2010 | Laugharn, Jr. | B01F 11/0283 |
| | | | 366/127 |
| 7,942,568 B1 | 5/2011 | Branch et al. | |
| 8,636,032 B2 * | 1/2014 | Burns | F04B 17/00 |
| | | | 137/828 |
| 8,659,753 B1 * | 2/2014 | Cabalo | G01J 1/4257 |
| | | | 356/213 |
| 2002/0124879 A1 * | 9/2002 | Kaplan | B01L 3/50273 |
| | | | 137/13 |
| 2004/0040379 A1 * | 3/2004 | O'Donnell | A61B 5/0095 |
| | | | 73/627 |
| 2005/0020945 A1 | 1/2005 | Tosaya et al. | |
| 2008/0070195 A1 | 3/2008 | Divito et al. | |
| 2009/0103083 A1 * | 4/2009 | Kremeyer | G01N 21/1702 |
| | | | 356/317 |
| 2009/0220908 A1 | 9/2009 | Divito et al. | |
| 2010/0330539 A1 | 12/2010 | Glover et al. | |
| 2012/0204648 A1 * | 8/2012 | Wang | A61B 5/0095 |
| | | | 73/606 |
| 2013/0338478 A1 * | 12/2013 | Hirota | A61B 8/429 |
| | | | 600/407 |
| 2015/0056567 A1 | 2/2015 | Fregoso et al. | |
| 2015/0151380 A1 * | 6/2015 | Hosseini | B23K 26/009 |
| | | | 428/600 |
| 2016/0356746 A1 * | 12/2016 | Piestun | A61B 5/0095 |
| 2017/0176393 A1 * | 6/2017 | O'Donnell | G01N 29/46 |
| 2017/0273568 A1 * | 9/2017 | Miyasato | A61B 5/0095 |
| 2018/0011031 A1 * | 1/2018 | Maznev | G01N 21/9515 |
| 2018/0292309 A1 * | 10/2018 | Prasad | G01N 21/1702 |
| 2019/0204275 A1 * | 7/2019 | Hatahori | G01B 9/02098 |
| 2019/0257795 A1 * | 8/2019 | Hirota | G01N 29/14 |

* cited by examiner

PHOTOACOUSTIC LAYER DISPOSED ON A SUBSTRATE GENERATING DIRECTIONAL ULTRASOUND WAVES

CROSS-REFERENCE TO RELATED APPLICATIONS

The present application claims the benefit of U.S. Provisional Application No. 62/461,371, filed Feb. 21, 2017, entitled "Laser Streaming: Turning A Laser Beam Into A Liquid Jet," which is hereby incorporated herein by reference in its entirety for all purposes.

BACKGROUND

The process of converting (or transforming) one form of energy into another is often referred to as transduction. A transducer is a device that is typically employed to perform such a function, and transducers can be characterized by the direction in which physical system (e.g., pressure, temperature, sound waves, etc.) passes through them. For example, a sensor is a type of transducer that receives and responds to a signal/stimulus from a physical system (e.g., temperature) and produces an electrical signal that represents information about the physical system. An actuator, on the other hand, is a transducer that controls/generates a physical system (e.g., sound waves), in response to some electrical signal. For example, a speaker transforms an electrical signal of a recording to mechanical sound waves.

SUMMARY OF THE DISCLOSURE

In accordance with at least one example, a system comprising a substrate having a first side and a second side; and a layer of photoacoustic material disposed on the first side of the substrate, the layer of photoacoustic material being configured to generate a directional ultrasound wave in response to a laser beam impinging on the layer.

In accordance with another example, a microfluidics laser streaming device, comprising a housing; a substrate coupled to the housing and having a first side and a second side, the second side positioned to receive a laser beam; a layer of photoacoustic material disposed on the first side of the substrate, the layer of photoacoustic material being configured to generate a directional ultrasound wave in a direction away from the first side in response to a laser beam impinging on the layer; and a conduit coupled to the housing and having an opening adjacent to the layer of photoacoustic material.

In accordance with yet another example, a method of generating a directional ultrasound wave, comprising: directing a laser beam at a photoacoustic layer positioned on a substrate; and generating the directional ultrasound wave in response to the laser beam striking the photoacoustic layer.

BRIEF DESCRIPTION OF THE DRAWINGS

For a detailed description of various examples, reference will now be made to the accompanying drawings in which.

DETAILED DESCRIPTION OF DISCLOSED EXEMPLARY EMBODIMENTS

As noted above, one form of energy can be transformed into another. These energy forms may include, for example, mechanical, electrical, chemical, electromagnetic, thermal, and acoustic energy. Research has been conducted to explore transforming other forms of energy, such as, transforming light energy (or in other words, high-energy photons) to mechanical energy. Transforming light energy into some form of mechanical energy requires efficient momentum transfer, and that is difficult to attain. An efficient system that can perform such a transformation is desired.

As disclosed herein, focusing a pulsed laser beam into water through a glass window that includes a layer of light absorbing photoacoustic material can generate a liquid jet in the water that moves in the direction of refraction of the laser beam. Without being held to any particular theory or scientific principal, it is believed that the formation of the liquid jet is facilitated by the formation of ultrasound waves, at least in part, by the light absorbing photoacoustic material disposed on the glass window. Accordingly, at least some of the examples disclosed herein are directed towards transforming light energy to mechanical energy. In particular, the examples disclosed herein describe transforming the photonic energy of a light (e.g., a laser beam) into ultrasound waves. As further described below, this light to mechanical energy transformation can be used in a variety of valuable applications including, for example, generating liquid jets, which is sometimes herein referred to as laser streaming.

Figure 1:
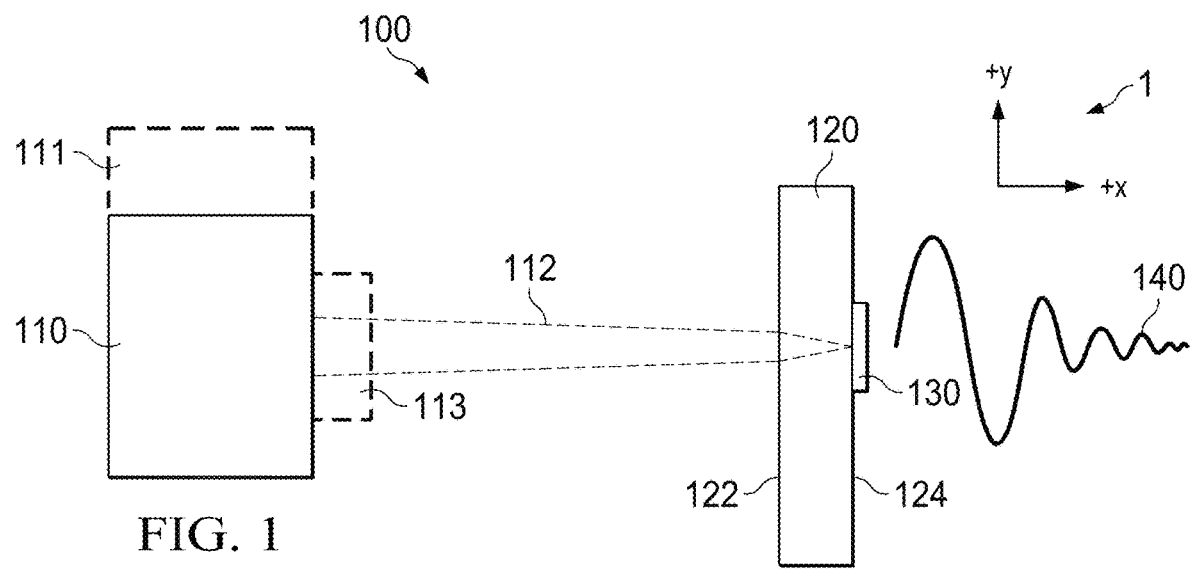
FIG. 1 is a schematic view of an illustrative system for generating directional ultrasound waves, in accordance with various examples.

FIG. 1 shows an illustrative system 100 for generating a directional ultrasound wave 140 propagating in +x-direction. Also depicted in FIG. 1 is a coordinate system 1, where the +x-axis and the +y-axis of the coordinate system 1 each lie in the plane that contains the page of the drawing. The system 100 includes a laser beam generator 110, which generates the laser beam 112. The system 100 also includes an optically transparent substrate 120 that has a first side 122 and a second side 124. In some examples, the optically transparent substrate 120 is configured to receive the laser beam 112 and refract the laser beam 112 to a photoacoustic layer 130 that is disposed on the second side 124 of the optically transparent substrate 120. The disposition of the photoacoustic layer 130 is not limited to the second side 124. In some examples, the photoacoustic layer 130 may be positioned on the first side 122, and in such examples, the laser beam 112 may directly incident on the photoacoustic layer 130. In other examples, the photoacoustic layer 130 may be positioned on both the first side 122 and the second side 124, and in such examples, the laser beam 112 may incident on either side of the optically transparent substrate 120 to generate directional ultrasound waves in the direction in which the laser beam 112 is propagating.

In some examples, the laser beam generator 110 generates pulsed laser beams. In some examples, each pulse generated by the laser beam generator 110 can be of a finite power (e.g., 200 mW) and is generated at a finite repetition rate (e.g., 1000 pulses per second) with each pulse lasting a finite time (e.g., 200 ns) In some examples, laser beam generator 110 is a pulsed laser diode beam generator and is employed to generate pulsed laser beams. In other examples, other types of pulsed laser beam generators, such as q-switched laser beam generator may be used. In some examples, the laser beam generator 110 may also include a controller unit 111 that is configured to control the repetition rate of pulsed laser beams. For example, for a laser beam generator 110 having a default repetition rate of the laser beam 112 of 1000 pulses per second, a controller unit 111 can both reduce the repetition rate, for instance, to 600 pulses per second, and can increase the repetition rate, for instance, to 1300 pulses per second.

In some examples, the laser beam generator 110 also includes one or more optical components 113, such as lenses (convex/concave lenses), prisms, etc. The optical components 113, if present in an example, may facilitate focusing (or converging) the laser beam 112 to a target (which, in this case, is the photoacoustic layer 130). In some examples, the optical components are housed inside the laser beam generator 110, but in other examples, are externally present between the laser beam generator 110 and the optically transparent substrate 120 as shown in FIG. 1. The optically transparent substrate 120 may include (but is not limited to) glass, quartz, rutile, zinc oxide, etc. In some examples, the optically transparent substrate 120 may bend (or refract) the laser beam 112 when it enters the optically transparent substrate 120. As used herein, the term "optically transparent" means greater than 70% transparent.

The photoacoustic layer 130 may include plasmonic nanoparticles, such as gold nanoparticles, silver nanoparticles, copper nanoparticles, etc. Plasmonic nanoparticles are particles whose conduction electrons can collectively oscillate at specific wavelengths when they interact with electromagnetic radiation of wavelengths that are larger than the diameter of the nanoparticles. Therefore, in some examples, the wavelength of the laser beam 112 depends on the size of nanoparticles. For example, gold nanoparticles of diameter 50 nm are driven into oscillation (due to strong coupling referred to as plasmonic resonance) when a laser beam of 527 nm wavelength is incident on the gold nanoparticles and gold nanoparticles of 60 nm are driven into oscillation at 540 nm. At plasmonic resonance wavelengths, plasmonic nanoparticles exhibit strong absorption of the incident light, which results in the conversion of the absorbed light into heat energy. This conversion is sometimes herein referred to as photothermal mechanism. When the temperature of the plasmonic nanoparticles changes, the surrounding media (e.g., air, water) may experience a similar temperature change. The plasmonic nanoparticle and the media surrounding it expand during the irradiation of the laser beam, and contract after the pulse has passed, generating ultrasound wave. In other words, the photothermal mechanism results in temporal changes of the temperatures of the plasmonic nanoparticles, which expand and contract the nanoparticles (following these temperature changes), which further translate into pressure change. In examples where the media surrounding the photoacoustic layer 130 is a liquid, microbubbles may form in the liquid when the laser beam 112 is incident on the photoacoustic layer 130. The formation of these microbubbles may result in the generation of ultrasound waves, but unlike the ultrasound waves generated by the interaction of the laser beam 112 and the photoacoustic layer 130, the ultrasound waves generated by the microbubbles are not focused in a single direction.

In some examples, the photoacoustic layer 130 may depend on the type of nanoparticle used in the photoacoustic layer 130. For example, the plasmonic resonance frequency of gold nanoparticles is in the range of 520 nm to 900 nm and the plasmonic resonance frequency of silver nanoparticles is in the range of 400 nm to 900 nm.

The photoacoustic layer 130 can include material that can thermally expand and contract when exposed to certain wavelengths. In some examples, the photoacoustic layer 130 may include graphene, graphene oxide, carbon nanotubes, etc. In other examples, the photoacoustic layer 130 may include transition metal chalcogenides, such as molybdenum diselenide, tungsten disulfide, molybdenum disulfide, etc. Because the absorption of the incident light depends on the wavelength of the light impinging the photoacoustic layer 130, the wavelength of the laser beam 112 depends at least in part on the type of the photoacoustic layer 130 (e.g., 527 nm for gold nanoparticles and 430 nm for silver nanoparticles). The photoacoustic layer 130, depending on the type of material in the layer, can be deposited or transferred or implanted on the optically transparent substrate 120 in a variety of means. For example, multilayer graphene can be grown on a copper film and then transferred to the optically transparent substrate 120, whereas carbon nanotubes can be deposited or grown directly on the optically transparent substrate 120. Nanoparticles, on the other hand, may be implanted in the optically transparent substrate using an ion implantation device. The photoacoustic layer 130 fabricated using nanoparticles may appear to be positioned in the optically transparent substrate 120. However, in this disclosure, photoacoustic layers claimed or described as being "on" the optically transparent substrate 120 means and include photoacoustic layers that are supported by or mounted to a substrate 120 by any means, and include the case where the layers engage an outer surface of the substrate and also where they are embedded within the substrate.

Referring still to FIG. 1, system 100 is shown to generate the directional ultrasound wave 140. In one embodiment, the optically transparent substrate 120 is glass; the photoacoustic layer 130 includes gold nanoparticles, which are implanted in a portion of the glass using an ion implantation system, such as NEC Mino-Tandem 5.1 MeV Ion Accelerator. The laser beam generator 110 focuses a single pulse of the laser beam 112 of 527 nm wavelength that enters from the first side 122 of substrate 120 and refracts to the photoacoustic layer 130. As described above, the laser beam 112 is focused to the photoacoustic layer 130 using the optical components, such as lenses, which may be present in the laser beam generator 110 or can be externally present between the laser beam generator 110 and the optically transparent substrate 120. The optically transparent substrate 120 refracts the laser beam 112.

As the laser beam 112 strikes the photoacoustic layer 130, the photoacoustic layer 130, due to the photothermal mechanism described above, absorbs at least some of the laser beam 112 and begins to thermally expand and contract. As the photoacoustic layer 130 is positioned on the substrate 120, the thermal expansion and contraction of the photoacoustic layer 130 vibrate a portion of the substrate 120, which generates the directional ultrasound wave 140 propagating in the +x-direction. Stated another way, the presence of the photoacoustic layer 130 on the substrate 120, and the thermal expansion/contraction resulting from the absorption of the laser beam 112 produces the ultrasound wave 140 traveling away from the second side 124 in the direction of propagation of the laser beam 112.

Figure 2A:
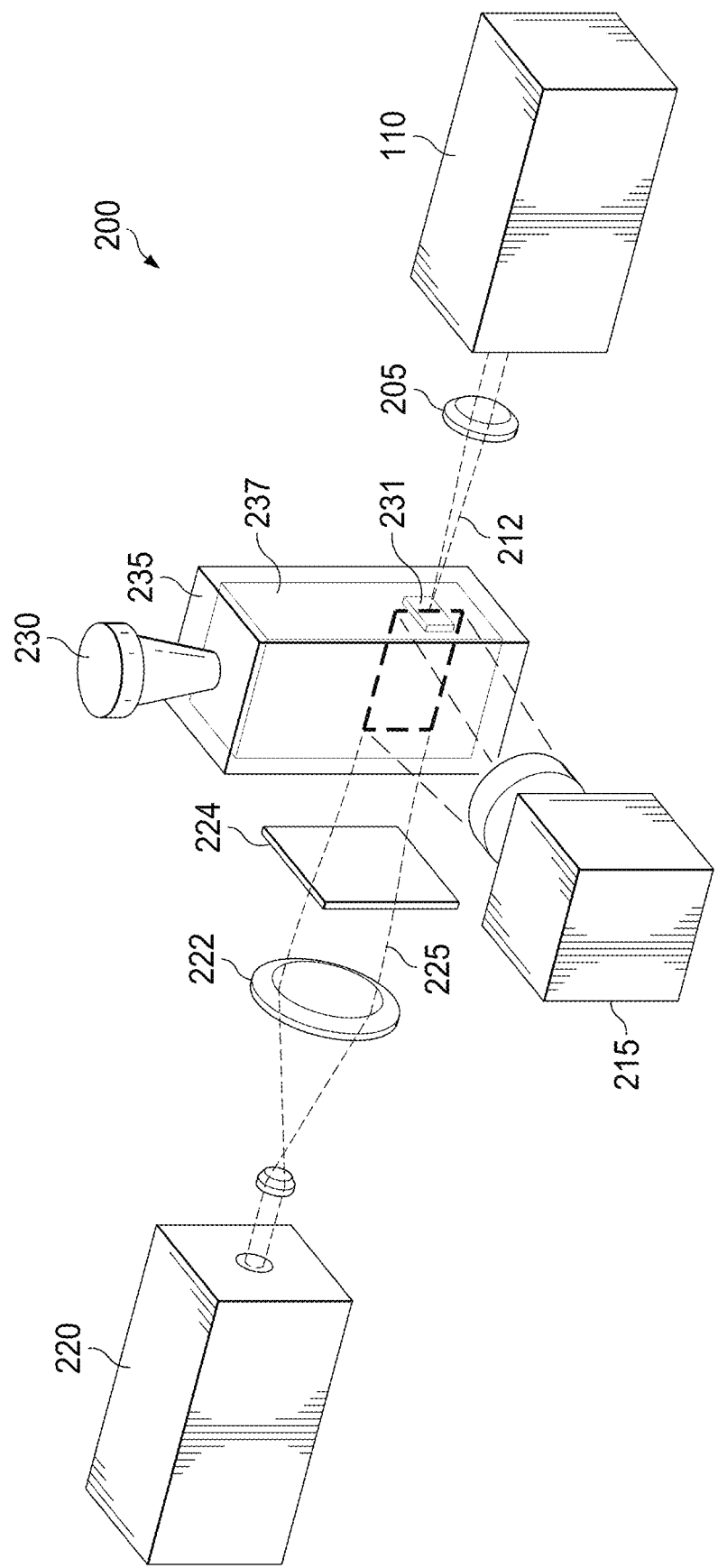
FIG. 2(a) is a perspective view of a system used to generate and capture a jet flow, in accordance with various examples.

Now referring to FIG. 2(a), a perspective view of a system 200 that was used to generate and capture a jet flow formed by the generation of directional ultrasound waves. The system 200 included the laser beam generator 110, which focused the laser beam 212 with an external lens 205 (converging lens with 10 cm focal length). The laser beam 212 focused to a photoacoustic layer 231 disposed on the inner wall of a glass cuvette 235. In this setup, the laser beam 212 was a 527 nm pulsed laser with a pulse width of 150 nanoseconds at a 1 kHz repetition rate (i.e., 1000 pulses in 1 second). The glass cuvette 235 of 1 mm thickness was filled with deionized water 237. A camera 215 and another laser 220 were included in the setup 200 to take clear snapshots of the jet produced. The setup 200 also included cylindrical lenses 222, 224 to focus the laser 220. Additionally, polymer microspheres were added to the water to facilitate visualizing the liquid jet flow. A hydrophone (V312-SU-F0.46-IN-PTF from Olympus, 10-MHz bandwidth) was used to detect the directional ultrasound waves generated when the laser beam 212 impinged on the photoacoustic layer 231.

Upon focusing the laser beam 212 at the photoacoustic layer 231, directional ultrasound wave, such as the directional ultrasound wave 140 described in FIG. 1, is generated in the glass cuvette 235. In response to the generation of the directional ultrasound waves, a liquid jet is generated. The formation of the liquid jet is a consequence of energy transformation between propagating directional ultrasound waves and the liquid. Stated another way, as the directional ultrasound flows, it attenuates as it exchanges energy with the liquid, which generates the liquid jet. The flow of liquid jet is proportional, at least in part, to the rate of attenuation of the directional ultrasound waves.

Figure 2B:
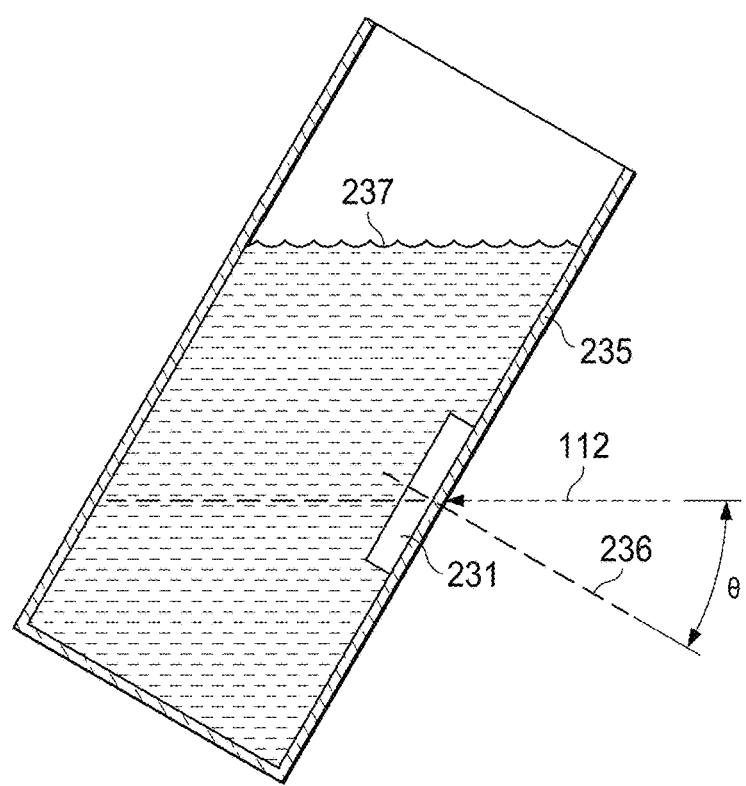
FIG. 2(b) shows the angle of incidence of the laser beam to the glass cuvette, in accordance with various examples.
Figure 2C:
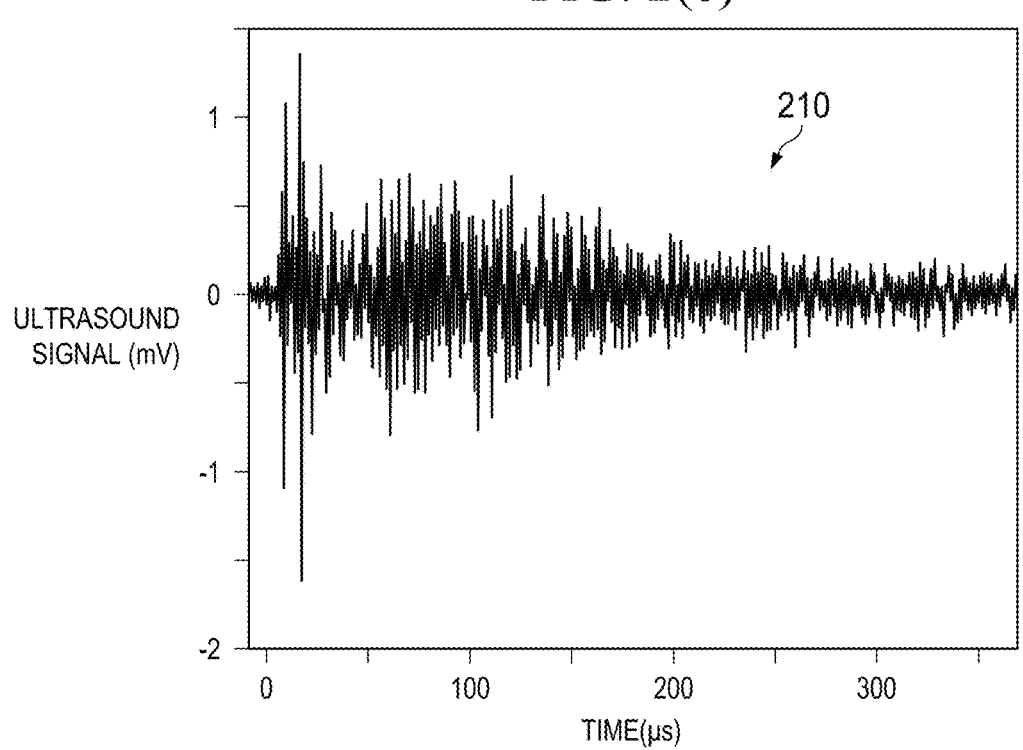
FIG. 2(c) is a graph of an illustrative directional ultrasound wave generated by a single pulse of a laser beam, in accordance with various examples.
Figure 2D:
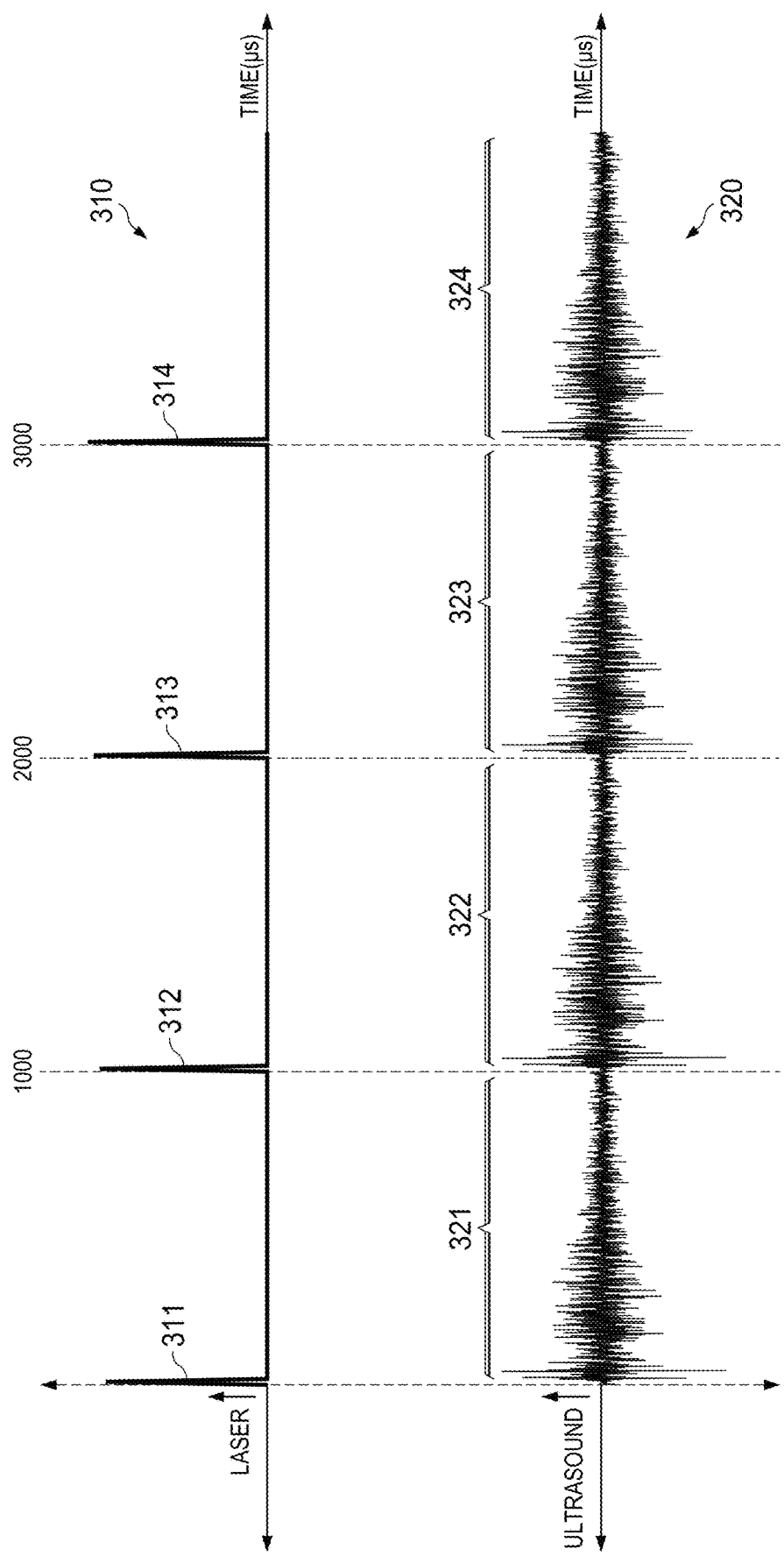
FIG. 2(d) is a graph of illustrative directional ultrasound waves generated by sending a series of pulsed laser to the photoacoustic layer, in accordance with various examples.
Figure 2E:
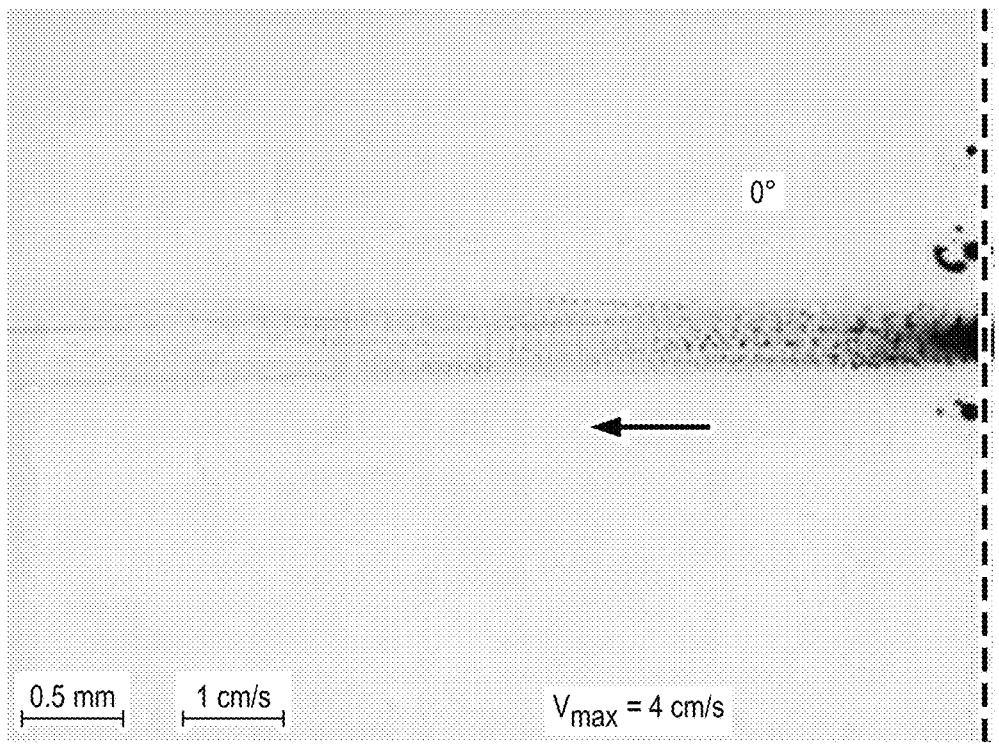
FIGS. 2(e)-2(h) are snapshots showing a liquid jet flow in the glass cuvette, in accordance with various examples.

Now referring to FIG. 2(c), a graph 201 depicting directional ultrasound wave 210 that was generated by a single pulse of a laser beam in the setup 200. The x-axis depicts time (microseconds) and the y-axis depicts the ultrasound signal (mV). Upon impinging a laser beam 212 of pulse duration 150 ns, a directional ultrasound wave 210 lasting more than 300 microseconds was captured by the hydrophone 230. Now briefly referring to FIG. 2(d), a graph 320 of illustrative directional ultrasound waves generated by sending a series of pulsed laser to the photoacoustic layer with a pulse width of 150 nanoseconds (at a 1 kHz repetition rate.) The graph 310 shows pulses 311, 312, 313, 314 of a laser beam that may be repetitively generated after 1000 microseconds. The graph 320 depicts the directional ultrasound waves 321, 322, 323, 324 may be generated after pulses 311, 312, 313, 314, respectively, strike the photoacoustic layer 130. For example, the pulse 311 of the laser beam generated at t=0 further generates the directional ultrasound wave 321, and the pulse 312 generated at t=500 us further generates the directional ultrasound wave 322.

FIGS. 2(e)-2(h) shows snapshot of a liquid jet flow occurred when the laser beam 212 a pulse width of 150 nanoseconds at a 1 kHz repetition rate was focused on the photoacoustic layer 231 in the glass cuvette 235. The exposure time for each shot was 100 ms. The white dashed line indicates the cuvette 235 surface, and the block arrows indicate the direction of flow of liquid jet and the laser propagation. The maximum speed observed of the liquid jet flow at 0° angle of incidence (FIG. 2(e)) was 4 cm/s with a 120 mW laser beam 212. The speed of the jet flow was controlled by varying the angle of incidence of the laser beam 212 hitting the photoacoustic layer 231. Referring briefly to FIG. 2(b), illustrates the angle of incidence of the laser to the glass cuvette 235. The angle of incidence may be defined as the angle between the line of incidence of the laser beam 212 and a line normal to the surface of the glass cuvette 235 at the point of incidence of the laser beam 212.

Figure 2F:
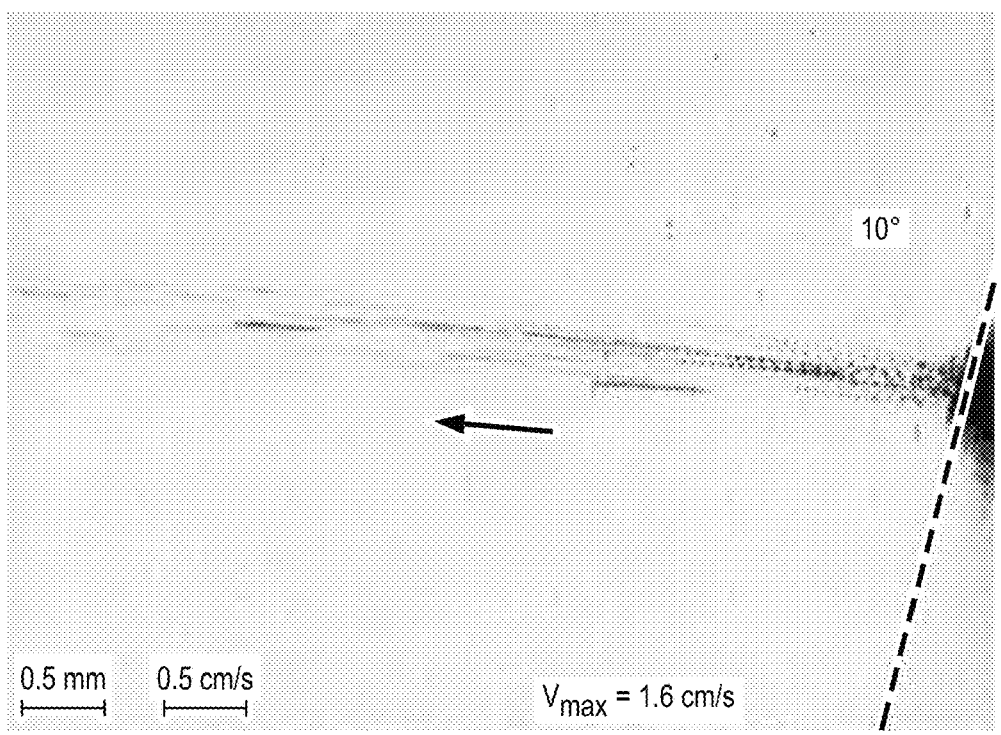
Figure 2G:
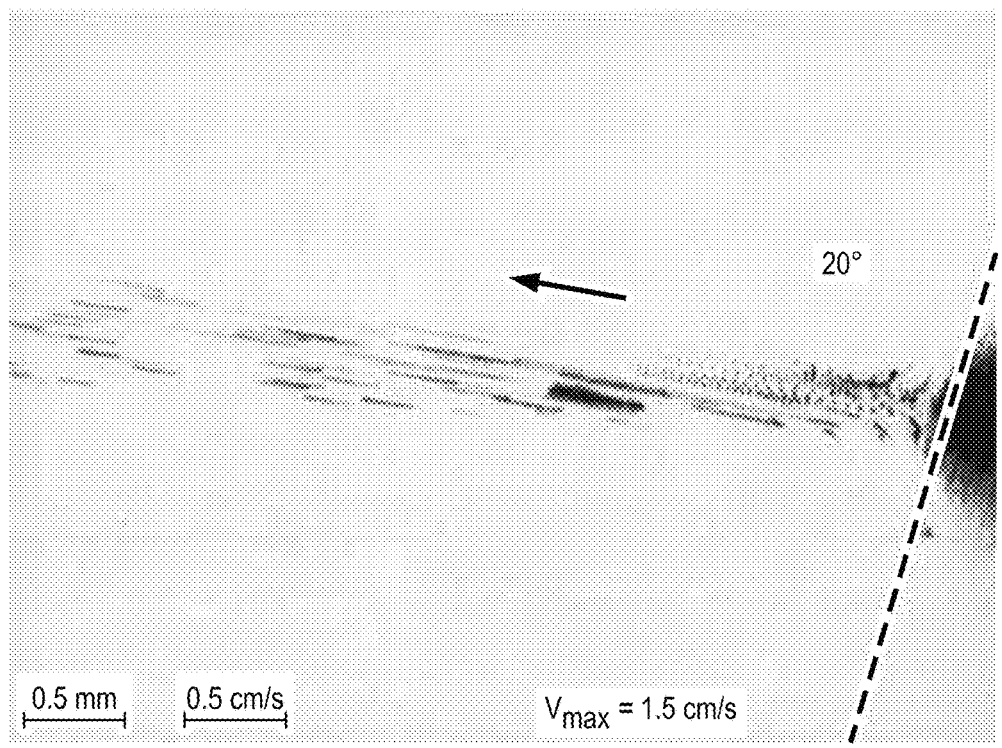
Figure 2H:
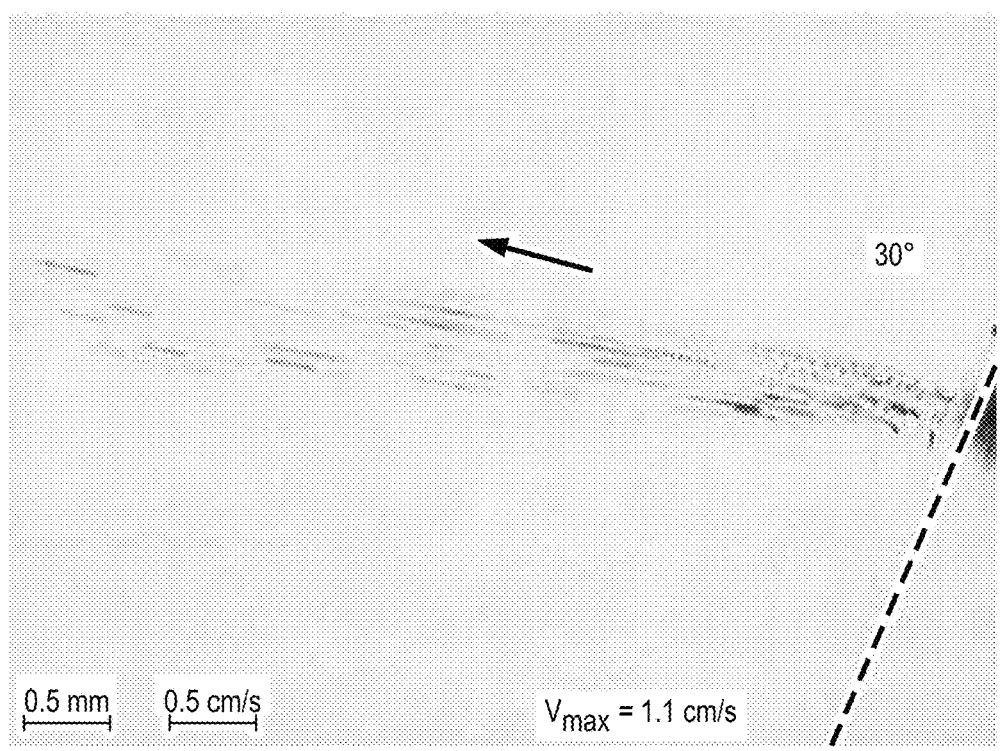

Owing to the reduced propagation energy of the directional ultrasound waves, the jet flow speed reduces at finite (greater than zero) angle of incidence. For example, FIGS. 2(e)-2(h) also shows the speed of the jet flow at different angles of incidences. FIG. 2(f) shows the maximum speed of 1.6 cm/s at 10°; FIG. 2(g) shows the maximum speed of 1.5 cm/s at 20°; FIG. 2(h) depicts the maximum speed of 1.1 cm/s at 30°.

Figure 3:
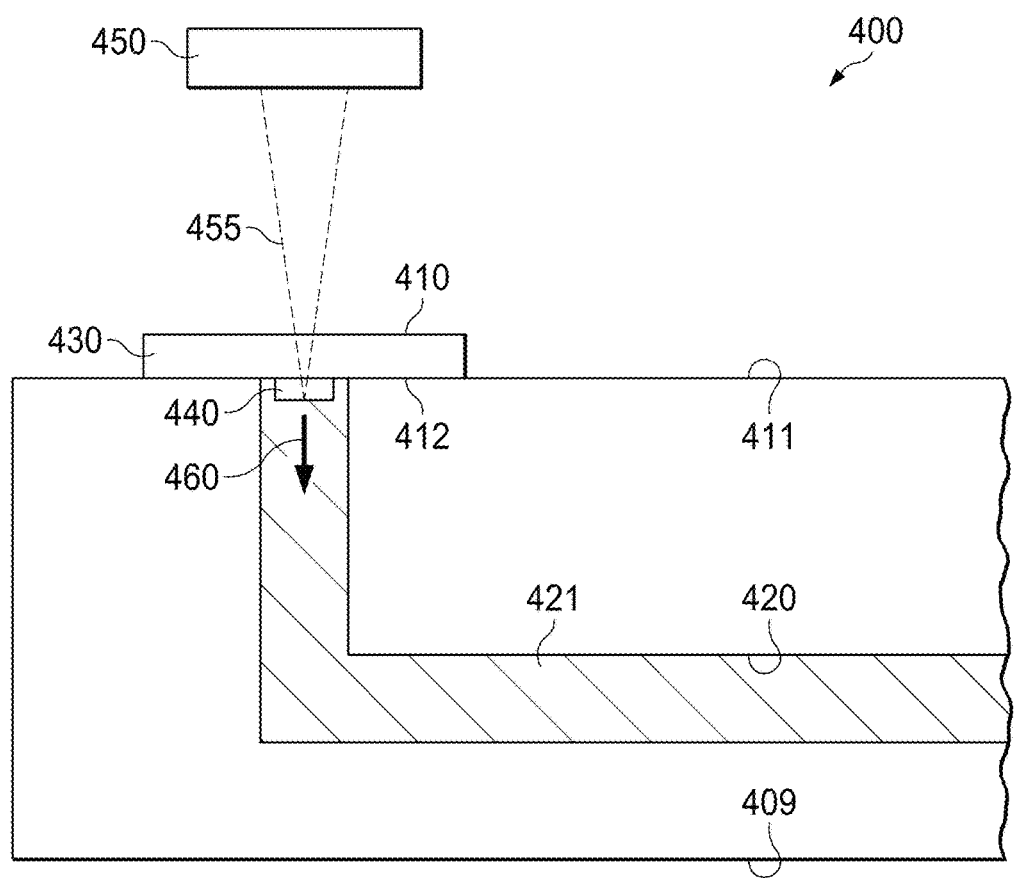
FIG. 3 is a cross-section of a portion of an exemplary microfluidics device, in accordance with various examples.

As noted from the experiment setup 200 and its results, the directionality and the propagation energy of one or more ultrasound waves can be harnessed and be further transformed into continuous jet flow, which can be used in valuable applications, such as microfluidics. FIG. 3 shows a cross-sectional view of a portion of an exemplary microfluidics device 400 used to (but not limited to) perform a medical test. FIG. 3 depicts a portion of such a microfluidics device 400. The microfluidics device 400 may be a closed system such that the liquid 421 circulates or the fluid 421 flows in the conduit 420. In some examples, the liquid 421 may flow into different container or into a different conduit (not expressly shown).

As shown the microfluidics device 400, a housing 409 that has a top side 411 and includes a conduit 420 coupled to the housing 409. In some examples, the housing 409 includes Polydimethylsiloxane (PDMS). The shape of the conduit 420 is not limited to the "L" shape depicted in FIG. 4. The conduit 420, in some examples, is filled with a liquid 421, which can be water. The microfluidics device 400 further includes a substrate 430 coupled to the housing 409 and having a first side 410 and a second side 412, where a layer of photoacoustic material 440 is disposed on the second side 412 of the substrate 430. FIG. 3 depicts the substrate 430 extending on a portion of the housing 409. In some examples, the substrate 430 may extend on the top side 411 of the housing 409. In some examples, the conduit 420 has an opening adjacent to the layer of photoacoustic material 440. Stated another way, the substrate 430 is positioned on the top side 411 such that the photoacoustic material 440 is facing the opening of the conduit 420. The microfluidics device 400 further includes a laser beam generator 450, similar to the laser beam generator 110 (described in FIG. 1), and generates a laser beam 455. In some examples, the first side 410 is configured to receive the laser beam 455.

In the example, where the conduit 420 is filled with a liquid 421, such as water, upon focusing one or more laser beams 455 at the substrate 430, directional ultrasound waves (similar to those described generated in the system 200), are generated in the conduit 420. In response to the generation of the ultrasound waves, liquid jet 460 is generated in the conduit 420. As noted above, in examples where the media surrounding the photoacoustic layer is a liquid, microbubbles may form in the liquid when the laser beam is incident on the photoacoustic layer 130. The formation of these microbubbles may result in the generation of ultrasound waves, but unlike the ultrasound waves generated by the interaction of the laser beam 455 and the photoacoustic layer 440, the ultrasound waves generated by the microbubbles are not focused in a single direction, and thus cannot result in a liquid flow.

In the foregoing discussion and in the claims, the terms "including" and "comprising" are used in an open-ended fashion, and thus should be interpreted to mean "including, but not limited to . . . ." The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

What is claimed is:

1. A system comprising:
   a substrate having a first side and a second side; and
   a layer of photoacoustic material disposed on the first side of the substrate, the layer of photoacoustic material being configured to generate a directional ultrasound wave in response to a laser beam impinging on the layer.

2. The system of claim 1, wherein the photoacoustic layer comprises nanoparticles.

3. The system of claim 2, wherein the nanoparticles includes noble metal nanoparticles.

4. The system of claim 2, wherein the photoacoustic layer is selected from a group consisting of carbon nanotubes, graphene, graphene oxide, molybdenum diselenide, tungsten disulfide, and molybdenum disulfide.

5. The system of claim 2, wherein the nanoparticles have a size that is smaller than or equal to a wavelength of the laser beam.

6. The system of claim 2, the nanoparticles are gold nanoparticles, wherein a plasmonic resonance frequency of the gold nanoparticles is in a range of 520 nm to 900 nm.

7. The system of claim 1, wherein a propagation energy of the directional ultrasound wave depends, at least in part, on an angle of incidence of the laser beam on the substrate.

8. The system of claim 1, wherein the substrate is configured such that a laser beam directed in a first direction enters the substrate from the second side and generates the ultrasound wave away from the first side and in the first direction.

9. The system of claim 1, wherein the substrate is configured such that a laser beam directed in a first direction directly strikes the photoacoustic layer on the first side and generate the directional ultrasound wave away from the second side and in the first direction.

10. The system of claim 1 further comprising a microfluidics channel, wherein the substrate is positioned adjacent to the microfluidics channel such that the directional ultrasound wave is configured to generate a liquid jet in the microfluidics channel.

11. The system of claim 1, wherein the substrate comprises glass.

12. The system of claim 1, wherein the laser beam is a pulsed laser beam.

13. A microfluidics laser streaming device, comprising:
    a housing;
    a substrate coupled to the housing and having a first side and a second side, the second side positioned to receive a laser beam;
    a layer of photoacoustic material disposed on the first side of the substrate, the layer of photoacoustic material being configured to generate a directional ultrasound wave in a direction away from the first side in response to a laser beam impinging on the layer; and
    a conduit coupled to the housing and having an opening adjacent to the layer of photoacoustic material.

14. The microfluidics laser streaming device of claim 13 further comprising a fluid in the conduit.

15. The microfluidics laser streaming device of claim 13 further comprising a laser beam generator configured to generate the laser beam.

16. The microfluidics laser streaming device of claim 13, wherein the photoacoustic material includes noble metal nanoparticles.

17. The microfluidics laser streaming device of claim 13, wherein the photoacoustic material is selected from a group consisting of carbon nanotubes, graphene, graphene oxide, molybdenum diselenide, tungsten disulfide, and molybdenum disulfide.

18. The microfluidics laser streaming device of claim 13, wherein the housing comprises Polydimethylsiloxane (PDMS).

19. The microfluidics laser streaming device of claim 13, wherein the laser beam is a pulsed laser beam.

20. The microfluidics laser streaming device of claim 13, wherein the substrate comprises glass.

21. A method of generating a directional ultrasound wave, comprising:
    directing a laser beam at a photoacoustic layer positioned on a substrate; and
    generating the directional ultrasound wave in response to the laser beam striking the photoacoustic layer.

22. The method of generating the directional ultrasound wave of claim 21, further comprising thermally expanding and contracting the photoacoustic layer in response to the laser beam striking the photoacoustic layer.

23. The method of generating the directional ultrasound wave of claim 21, further comprising using the directional ultrasound wave to generate a liquid jet in a liquid medium.

* * * * *